United States Patent
Hoagland et al.

(10) Patent No.: US 9,422,160 B1
(45) Date of Patent: Aug. 23, 2016

(54) METHOD OF MAKING A HYDROGEN SENSING PIGMENT

(75) Inventors: William Hoagland, Boulder, CO (US); David K. Benson, Golden, CO (US); Rodney D. Smith, Golden, CO (US)

(73) Assignee: Element One, Inc., Boulder, CO (US)

( * ) Notice: Subject to any disclaimer, the term of this patent is extended or adjusted under 35 U.S.C. 154(b) by 1248 days.

(21) Appl. No.: 13/166,777

(22) Filed: Jun. 22, 2011

Related U.S. Application Data

(63) Continuation-in-part of application No. 11/553,400, filed on Oct. 26, 2006, now abandoned.

(60) Provisional application No. 60/730,960, filed on Oct. 28, 2005.

(51) Int. Cl.
*B82Y 30/00* (2011.01)
*G01N 27/26* (2006.01)

(52) U.S. Cl.
CPC ............... *B82Y 30/00* (2013.01); *G01N 27/26* (2013.01)

(58) Field of Classification Search
None
See application file for complete search history.

(56) References Cited

U.S. PATENT DOCUMENTS

| | | | |
|---|---|---|---|
| 3,378,348 | A | 4/1968 | McConnaughey |
| 3,563,914 | A | 2/1971 | Wattemena |
| 4,948,496 | A | 8/1990 | Chand |
| 5,183,763 | A | 2/1993 | Mallow et al. |
| 5,338,430 | A | 8/1994 | Parsonage et al. |
| 5,858,307 | A | 1/1999 | Neihof |
| 6,277,589 | B1 | 8/2001 | Seibert et al. |
| 6,420,181 | B1 | 7/2002 | Novak |
| 6,448,068 | B2 | 9/2002 | Seibert et al. |
| 6,936,223 | B2 | 8/2005 | Lippold et al. |
| 6,939,717 | B2 | 9/2005 | Jiang et al. |
| 6,969,613 | B1 | 11/2005 | Ebinuma et al. |
| 7,560,160 | B2 | 7/2009 | Sudarshan et al. |
| 8,003,055 | B1 | 8/2011 | Muradov |
| 2004/0050143 | A1 | 3/2004 | Hoagland |
| 2005/0092761 | A1 | 5/2005 | Marganski |
| 2007/0251822 | A1 | 11/2007 | Hoagland et al. |

FOREIGN PATENT DOCUMENTS

| | | | |
|---|---|---|---|
| JP | 2005-331364 | * | 12/2005 |
| JP | 2005-345338 | * | 12/2005 |

OTHER PUBLICATIONS

W. Hoagland et al., Novel Wide-Area Hydrogen Sensing Technology, 16 WHEC 1-12 (2006).*
C.-J. Hou et al., Preparation and Characterization of WO3 Nano-powder with Microemulsion Method, 2nd IEEE Int'l Nanoelectronics Conf. 362-365 (2008).*
S. Wang et al., Visible Light-Driven Photodecomposition System: Preparation and Application of Highly Dispersed Pt-Loaded WO3 Microparticles, 6 Micro & Nano Lett. 229-232 (2011).*
J. S. Suehie et al., "Tin Oxide Gas Sensor Fabricated Using CMOS Micro-Holplates and In Situ Processing" IEEE Electron Device Letters 14, 1993, pp. 118-120.
S. Semancik et al., "The Use of Surface and Thin Film Science in the Development of Advanced Gas Sensors," Appl. Surf. Science 70/71, 1993, pp. 337-346.
R. E. Cavicchi et al., "Fast Temperature Programmed Sensing for Microhotplate Gas Sensors," IEEE Electron Device Letters 16, 1995, pp. 286-288.
R. E. Cavicchi et al., "Growth of SnO2 Films on Micro-machined Hotplates," Applied Phys. Letters 66 (7), 1995, pp. 812-814.
C. L. Johnson et al., "Integrated Ultra-thin-film Gas Sensors", Sensors and Actuators B (20), 1994, pp. 55-62.
X. Wang et al., "Monolithic Thin Film Metal Oxide Gas Sensor Arrays With Application to Monitoring of Organic Vapors," Sensors and Actuators B (28), 1195, pp. 63-70.
N. R. Swart et al., "Design Optimization of Integrated Micro-hotplates," Sensors and Actuators A (43), 1994, pp. 3-10.
N. Najafi et al., "A Micromachined Thin Film Gas Sensor." IEEE Electron Device Letters 4 (10). 1994, pp. 1770-1779.
F. DiMeo Jr., et al., "MOCVD of SnO2 on Silicon Micro-hotplate Arrays for Use in Gas Sensing Application," Mat. Res. Soc. Symp. Proc. 415; 1996, pp. 231-236.
International Search Report for PCT/US08/85029, ISA/US, Mar. 24, 2009.

* cited by examiner

*Primary Examiner* — Randy Boyer
(74) *Attorney, Agent, or Firm* — James R. Young; Cochran Freund & Young LLC

(57) ABSTRACT

Pigments comprising chemochromic metal oxide microparticles or nanoparticles the surfaces of which are superficially coated with nanoparticles of catalyst material. The pigments are prepared by mechanical or wet chemical processes.

5 Claims, 8 Drawing Sheets

METHOD OF MAKING A HYDROGEN SENSING PIGMENT

CROSS REFERENCES TO RELATED APPLICATIONS

This application is a continuation-in-part of U.S. patent application Ser. No. 11/553,400 filed Oct. 26, 2006 by William Hoagland et al. entitled "Visual Hydrogen Sensors Using Nanoparticles," which claims the benefit of U.S. Provisional Patent Application Ser. No. 60/730,960 filed Oct. 28, 2005 by William Hoagland et al. entitled "Hydrogen Indicating Pigments to Detect Hydrogen Gas." The entire contents of both of those applications are specifically incorporated herein by reference for all that they disclose and teach.

BACKGROUND OF THE INVENTION

Large quantities of hydrogen gas are used in numerous industries. Wherever hydrogen gas is used, detection of leaks is important. Most hydrogen gas detectors are large, bulky electronic devices that are capable of triggering safety devices such as shutoff valves and alarms. However, the international patent application no. PCT/US01/47151 (International Publication No. WO 02/46740 A1), entitled "Hydrogen Gas Indicator System", discloses a hydrogen gas indicator system that provides substrate materials that support hydrogen gas sensor materials with discrete indicia that provide information separate from any change in the physical properties of the hydrogen gas sensor itself. That hydrogen gas indicator system comprises a substrate material, a hydrogen gas sensor supported by the substrate material, a catalyst material that facilitates conversion of molecular hydrogen gas to atomic hydrogen, a molecular diffusion barrier which allows selectively permeable diffusion of the molecular hydrogen gas, and discrete indicia operably responsive to the hydrogen gas sensor. It also discloses a hydrogen gas indicator comprising a friable substrate material, a hydrogen gas sensor supported by the friable substrate material, a catalyst material that facilitates conversion of molecular hydrogen gas to the hydrogen gas, and a molecular diffusion barrier that allows selectively permeable diffusion of the molecular hydrogen gas.

The foregoing examples of the related art and limitations related therewith are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with systems, tools and methods which are meant to be examples and illustrative, not limiting in scope.

An embodiment of the present invention may therefore comprise a method of producing a hydrogen sensor coating including powder particles of chemochromic, transition metal oxide with a catalyst to create chemochromic powder pigments for use in paints, inks, dyes, and other emulsions that can be spread on surfaces to function as hydrogen detectors.

An embodiment of the present invention may further comprise a chemochromic powder pigment comprising powder particles of a transition metal oxide and a catalyst that is coated on or attached to surfaces of the transition metal oxide powder particles.

In addition to the example embodiments described above, further aspects and embodiments will become apparent by reference to the drawings and by study of the following descriptions.

BRIEF DESCRIPTION OF THE DRAWINGS

The accompanying drawings, which are incorporated herein and form a part of the specification, illustrate some, but not the only or exclusive, example embodiments and/or features. It is intended that the embodiments and figures disclosed herein are to be considered illustrative rather than limiting.

In the drawings.

DETAILED DESCRIPTION

Figure 1:
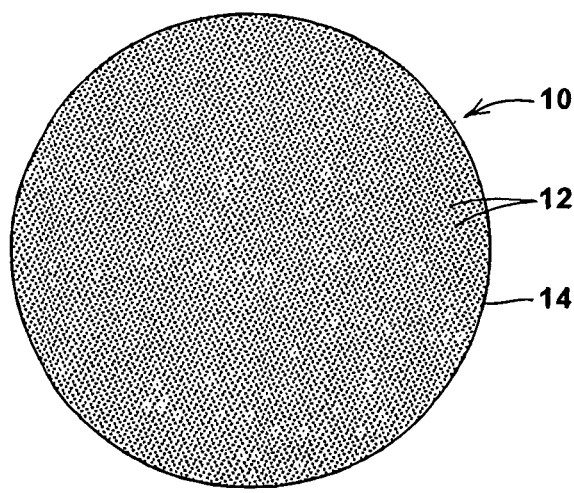
FIG. 1 is diagrammatic view of a metal oxide microparticle superficially coated with catalyst nanoparticles.

In accordance with one embodiment, visual hydrogen sensors can be made using microparticulate or nanoparticulate powders, i.e., discrete powder microparticles or nanoparticles of chemochromic material, such as tungsten oxide ($WO_3$), molybdenum oxide, or niobium oxide, that are superficially coated or aggregated in contact with a noble metal catalyst, such as platinum, palladium, ruthenium, or combinations of such metal catalysts. These transition metal oxide powder particles superficially coated with the noble metal catalysts can be used as pigments in paints, inks, dyes, powder coating materials, or other suspensions or mixtures that can be painted, sprayed, or applied in any other convenient manner onto surfaces, such as walls, badges, mechanical and electric equipment, or other devices to change color when exposed to hydrogen.

When the transition metal oxide microparticles that are coated with the catalyst are exposed to hydrogen gas, the catalyst causes the hydrogen gas molecules to dissociate into atomic hydrogen, which reduces the transition metal oxide to a lower oxidation state of the metal. Persons skilled in the art understand that a lower oxidation state means an oxidation state with fewer oxygen atoms in the compound than a higher oxidation state. For example, tungsten dioxide ($WO_2$) is a lower oxidation state of tungsten trioxide ($WO_3$). The reduction of the metal oxide to a lower oxidation state of the metal is manifested by a change in one or more physical properties of the transition metal oxide, such as color, light absorption, photoconductivity, electrical conduction, electrical resistivity, electro-capacitance, magneto-resistance, or optical properties. The change in such physical property or properties can be reversed by removing the transition metal oxide from exposure to hydrogen and by exposing the transition metal oxide to oxygen or to the partial pressure of oxygen available in a mixture of gases, thereby converting the transitional metal oxide back to its original metal oxide state. For example, tungsten trioxide ($WO_3$) is a chemochromic transition metal oxide that becomes noticeably darker in color upon conversion from a higher oxidation state of tungsten oxide, e.g., tungsten trioxide ($WO_3$), to a lower oxidation state of tungsten oxide, e.g., tungsten dioxide ($WO_2$). The partially reduced tungsten oxide absorbs light in the red portion of the visible spectrum so that white light falling on the tungsten oxide nanoparticles is reflected primarily in the blue portion of the spectrum. Therefore, under daylight or normal room lighting, the tungsten oxide is seen to change from a dull gray color to a bright blue when exposed to hydrogen. The color change is reversible upon removal or decreasing the concentration of the hydrogen and exposing the lower oxidation state of tungsten oxide to oxygen to convert it back to a higher oxidation state. As mentioned above, there are other chemochromic materials besides tungsten oxide that are well-known in the art and that can be used for the chemochromic hydrogen sensor material.

The metal oxide powder microparticles themselves are superficially coated with the catalyst to provide more speed and dramatic color change than the crumbled or broken substrate particles described in U.S. Pat. No. 6,895,805, issued May 24, 2005 to William Hoagland entitled "Hydrogen Gas Indicator System," (based on the International Application No. PCT/US01/47151, International Publication No. WO 02/46740), which is specifically incorporated herein by reference for all that it discloses and teaches. That patent application describes depositing a thin film layer of the transition metal oxide onto a friable substrate, followed by deposition of a thin film catalyst layer, and, optionally, a selective molecular diffusion barrier layer to form a hydrogen sensor and then crumbling or breaking the substrate with the several thin film layers into particles so that the particles of substrate support the hydrogen gas sensor materials. However, that kind of material, while functional, does not provide as much color change speed and intensity as desired for use as a pigment in hydrogen sensing paints, inks, dyes, and powder coating materials.

The color change speed and intensity can be increased significantly by increasing not only the surface area of the metal oxide that is exposed to hydrogen, but also the surface area interface between the catalyst and the metal oxide, by coating catalyst nanoparticles superficially onto discrete powder microparticles of the metal oxide itself, as opposed to the particles of crumbled or broken inert substrate material described in U.S. Pat. No. 6,895,805 issued to Hoagland that leaves a lot of inert substrate material bulk and inert substrate surface area in the pigment that is useless for hydrogen detection. In one embodiment, the hydrogen indicating pigments comprise fine particles of transition metal oxide, for example, tungsten oxide, molybdenum oxide, or niobium oxide, that have been superficially coated with a precious metal catalyst, for example, platinum, palladium, or ruthenium. The particle sizes of the metal oxide are very fine, typically less than 100 microns in diameter, and the catalyst nanoparticles are on the order of a few nanometers to a few tens of nanometers. For quantification, the catalyst particles include sizes in a range of two to thirty nanometers. In general, the catalyst particles can be of different sizes and shapes, but are very small compared to the metal oxide particles, e.g., diameters of one thousandth or less than the diameter of the metal oxide particles. As illustrated diagrammatically in FIG. 1, a pigment particle 10 with the distributed catalyst nanoparticles 12 on a much larger metal oxide microparticle 14 can be visualized somewhat like particles of sand superficially coated or sticking onto the surface of a beach ball. Generally, nanoparticles are considered to be particles in the range of one nanometer diameter to one micron diameter, and microparticles are considered to particles in the range of one micron to 1,000 microns.

We discovered, somewhat surprisingly, after experimenting with the wet chemical process described in the alternate wet chemical embodiment described below, that this result illustrated in FIG. 1 can also be obtained by a simple mechanical mixing process with commercially available metal oxide powders and "catalyst black" powder materials. The surprise was that the commercially available catalyst black powder material could be efficiently and sufficiently dispersed onto the fine, microparticles of the metal oxide by mixing them together and then grinding or milling them together. The very small catalyst nanoparticles stick to, and superficially coat, the surfaces of the larger metal oxide microparticles by van der Waals attraction forces, thus providing large surface area interfacing of catalyst with metal oxide that is durable and highly effective for use as a pigment for paints, inks, dyes, powder coats, etc., and that produce higher speed and intensity color changes when exposed to hydrogen than previous pigment particles, such as the crumbled or broken inert substrate-type particles described in U.S. Pat. No. 6,895,805 issued to Hoagland.

Producing hydrogen sensing pigment in this manner is also less complex and less expensive than previous hydrogen sensing pigment manufacturing processes and takes advantage of the fact that very fine particles of catalysts are commercially available as so-called "catalyst blacks". For example, the Chemical supplier, Alfa-Aesar headquartered in Ward Hill, Mass., markets a stock chemical Platinum-Ruthenium black which is a mixture of 50 atomic weight percent of platinum and 50 atomic weight percent of ruthenium, which is suitable for this pigment product and process. Numerous other suitable precious metal "blacks" are also available from a variety of commercial chemical supply companies because they are commonly used, for example, to catalyze various chemical reactions in chemical process industries and by research and development institutions. Microparticle powders of the chemochromic transition metal oxides are also available commercially. Any of the metal catalysts mentioned above can be used alone or in combinations with each other for purposes of this invention.

Example I

Figure 2:
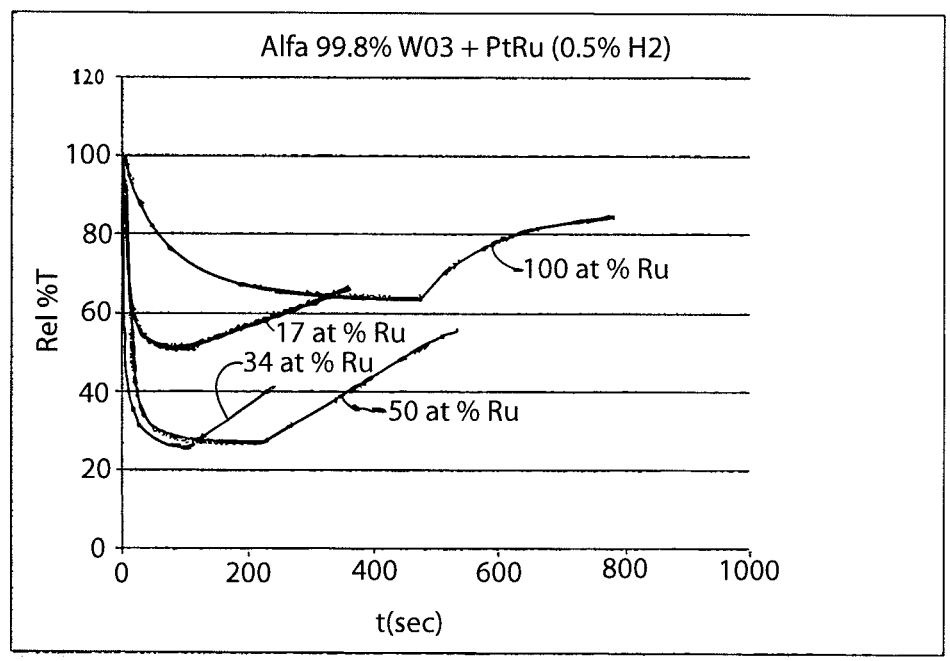
FIG. 2 is a graphical recording of optical transmittance for five pigments.

A commercially available fine powder of tungsten oxide was mixed with different commercially available platinum-ruthenium blacks. The oxide powder was carefully ground together with the catalyst black for a few minutes and then tested for the pigment's response to hydrogen gas. For these tests, the pigment was dispersed onto a fine filter paper where the fibers of the paper held the pigment in place. The optical transmittance through the filter paper and its coating of pigment was monitored in a specially designed sample holder as a dilute mixture of hydrogen gas in nitrogen gas (0.5 volume percent of hydrogen in nitrogen) was flowed over the pigment. FIG. 2 shows the change in optical transmittance as a function of time of hydrogen exposure for five different measurements of five different pigments. The five pigments differed from each other only in the ratio of platinum to ruthenium in the catalyst black (ranging from 17% ruthenium to 100% ruthenium). Each pigment became dramatically darker (i.e., the transmittance decreased) over a period of a few seconds to a few hundred seconds. After a few minutes, the flow of hydrogen gas mixture was replaced with a flow of air, and the recordings show an increasing optical transmittance as the pigment began to return to its original, nearly transparent, condition.

Figure 3:
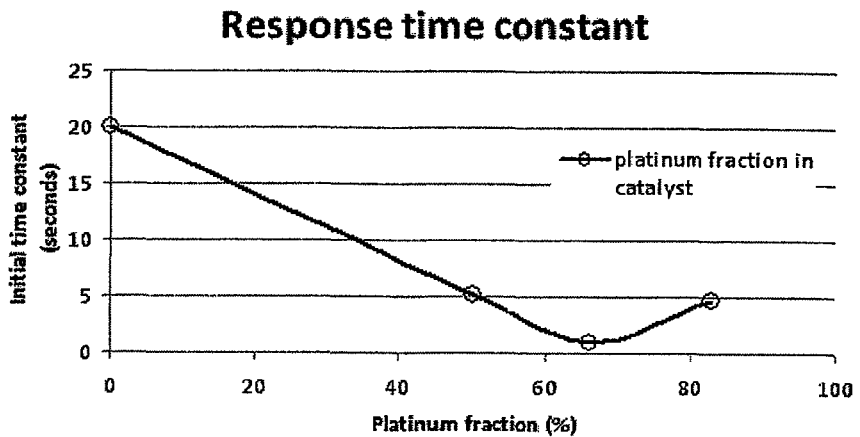
FIG. 3 is a graph of response time constant for platinum fractions in the catalyst.

The response curves in FIG. 2 were analyzed mathematically by curve-fitting the experimental curves to standard chemical kinetic mathematical functions. By this common technique, it is possible to calculate the response time constants (initial $t_1$ and final $t_2$) and extrapolate saturation ($Y_0$, the maximum percentage that the optical transmittance is reduced when the pigment response to hydrogen has saturated). The results for the initial response time constant and saturation coloration are shown in the table I below and in the graphs in FIGS. 3 and 4.

TABLE I

| Ru (at %) | Pt (at %) | Non-linear curve fit parameters | | | | | Saturation (%) |
|---|---|---|---|---|---|---|---|
| | | Y0 (%) | A1 (%) | A2 (%) | t1 (s) | t2 (s) | 100-Y0 |
| 17 | 83 | 50.3 | 37.5 | 12.2 | 4.7 | 24.5 | 49.7 |
| 34 | 66 | 26 | 49.1 | 24.9 | 0.9 | 16.3 | 74 |
| 50 | 50 | 26.8 | 52.7 | 20.6 | 5.2 | 25 | 73.2 |
| 100 | 0 | 63.7 | 10.2 | 26 | 20 | 90.3 | 36.3 |

Figure 4:
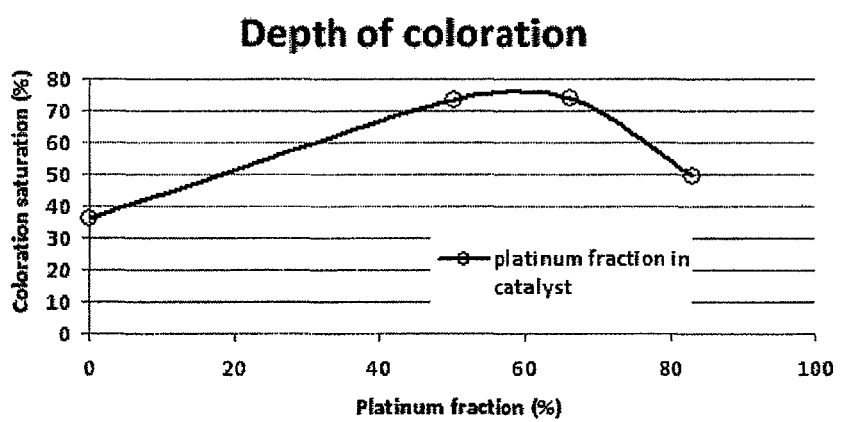
FIG. 4 is a graph of depth coloration for platinum fractions in the catalyst.

The desired result is a fast response (i.e., a small time constant) and a deeply colored pigment (i.e., a high percentage of coloration). In this particular example, the optimum mixture of platinum and ruthenium black appears to be about 60 percent platinum and 40 percent ruthenium in the mixed catalyst. The optimum in the curve shown in FIG. 4 is fairly flat, so a 50 percent platinum and 50 percent ruthenium option, which is commercially available as explained above, is a very good choice.

Generally, to meet the need for uniform distribution of the hydrogen sensing pigments in paints without roughness after the paints have dried on surfaces, the chemochromic pigment particles are made with powders of metal oxide particles 100 microns or smaller, for example, in a range of 10 to 100 microns. Inks are generally thinner and less viscous, so hydrogen sensing pigments for inks may better be made with powders of metal oxide particles in a range of 10 to 50 microns.

In another embodiment, a process of coating the microparticles or nanoparticles of tungsten trioxide or other transition metal oxide with a catalyst is described in the example II below with respect to platinum as the catalyst.

Example II

Hexachloroplatinic acid is used as a solution of soluble platinum. The hexachloroplatinic acid is then dissolved in a solvent, such as ethanol, acetone or isopropyl alcohol. The amount of hexachloroplatinic acid is adjusted so that the final concentration in the solvent is about one weight percent of a 5 gram sample of the tungsten trioxide powder microparticles or nanoparticles. For a 5 gram sample of the tungsten trioxide powder, a small amount of solvent is required. Typically, 10 to 15 ml of solvent is used to dissolve the acid. The tungsten trioxide powder is then added to the solution. The tungsten trioxide powder is soaked in the solution of solvent and hexochloroplatinic acid and placed in an oven at 60 to 70° Celsius to dry for approximately 16 hours. The microparticles or nanoparticles of tungsten trioxide are coated with the solution as the solvent is evaporated so that a chloroplatinate coating is formed on the surface of the individual tungsten trioxide microparticles or nanoparticles. The chloroplatinate is then reduced on the tungsten trioxide to platinum. This is done by placing the coated microparticles or nanoparticles of the tungsten trioxide in a tube furnace in an inert atmosphere. A forming gas, which is 10 percent hydrogen and 90 percent nitrogen, is passed over the coated microparticles or nanoparticles of tungsten trioxide at a flow rate of approximately 150 ml per minute. The oven is then ramped up to 300° C. over a period of approximately 2 hours. This process causes the palatinate, which is basically ionic and associated with a chloride, to be reduced to the platinum metal. The palatinate reduces on the tungsten trioxide microparticles or nanoparticles and forms multiple small metallic islands of platinum catalyst on the surface of these tungsten trioxide microparticles or nanoparticles. The initial microparticles or nanoparticles are highly colored because hydrogen from the forming gas reacts with the tungsten trioxide and reduces it to a lower oxide, e.g., tungsten dioxide, so they appear initially as a dark blue color. The furnace and the forming gas are then turned off, and the tungsten oxide powder coated with the islands of platinum is allowed to cool to room temperature in air, which reverses the color reaction, i.e., re-oxidized the lower oxide form of tungsten oxide back to the original tungsten trioxide form, and the platinum islands remain on the surface of the tungsten trioxide microparticles and nanoparticles. The resulting grayish or uncolored tungsten trioxide microparticles or nanoparticles coated with the islands of platinum will turn blue very quickly when re-exposed to hydrogen, and they are very useful as hydrogen sensing pigments for hydrogen indicating paints, inks, dyes, and powder coat products and applications.

Tungsten trioxide ($WO_3$) is a well known chromogenic material, i.e., $WO_3$, undergoes color changes under various circumstances. These color changes accompany a change in the oxidation state of some of the tungsten ions in the normally transparent crystalline $WO_3$. Partial reduction of the $WO_3$ changes some of the $W^{6+}$ ions to $W^{5+}$ ions. Because of the high dielectric constant of $WO_3$, a free electron in the vicinity of a $W^{5+}$ ion is trapped in a polarization field around the $W^{5+}$ ion. This kind of trapped electron is called a polaron and exhibits quantized optical absorption similar to those of orbiting electrons in a simple atom as disclosed by S. H. Joo, S. J. Choi, et al., "Ordered Nanoporous Arrays of Carbon Supporting High Dispersions of Platinum Nanoparticles." *Nature*, Vol. 412, pp. 169-172, Jul. 12, 2001. However, the interaction of the electron with the thermal vibrations of the $WO_3$ lattice spreads the optical transitions into a broad absorption band that peaks near 800 nm and extends into the red portion of the visible spectrum. Consequently, the partially reduced $WO_3$ appears blue.

The crystalline $WO_3$ can be partially reduced in numerous ways, i.e., by heating in a non-oxidizing atmosphere, electrochemically in a cell configuration, or by chemical reaction with a reducing agent such as lithium or hydrogen. Thin films of $WO_3$ have been used in various applications. In electrochromic windows the $WO_3$ film is reversibly darkened by applying a small voltage across a multi-layer thin film electrochemical cell made up of the $WO_3$, a solid electrolyte and a counter-electrode layer, all of which are applied to the window glass in a vacuum deposited multi-layer coating. In a similar application, "gasochromic" windows can be dimmed by reversibly introducing hydrogen gas into the sealed gap between glass panes of a sealed insulating glass window as disclosed by S. M. Lee, P. L. Hyeonsik, P. L. Cheong, D. Smith, C. E. Tracy, et al., "Gasochromic Mechanism in a-$WO_3$ Thin Films Based on Raman Spectroscopic Studies, *J. Applied Physics*, Vol. 88, No. 5, pp. 3076-3078, Sep. 1, 2000. A thin coating of $WO_3$ and platinum or palladium turns dark in the hydrogen gas. $WO_3$ thin films have also been used in various designs of hydrogen gas detectors including the authors' designs for a fiber-optic hydrogen detector as disclosed by D. K. Benson, C. Bechinger, and C. E. Tracy, "Fiber Optic Device for Sensing the Presence of a Gas," U.S. Pat. No. 5,708,735, Jan. 13, 1998, a bio-hydrogen screening device as disclosed by M. Seibert, D. K. Benson, and T. M. Flynn, "System for Rapid Biohydrogen Phenotype Screening of Microorganisms Using a Chemochromic Sensor," U.S. Pat. No. 6,448,068, Sep. 10, 2002, and a detector for hydrogen gas dissolved in welded metal as disclosed by R. D. Smith, D. K. Benson, et al., "The Determination of Hydrogen Distribution in High-strength Steel Weldments Part 2: Optoelectronic Diffusible Hydrogen Sensor," American Welding Society, http://files.aws.org/wj/supplement/SmithPart2-05-01/pdf. In each of these designs, a catalyst is applied to the thin film $WO_3$ to increase its reaction rate with hydrogen gas.

The powder microparticles or nanoparticles of chemochromic metal oxide that are coated or impregnated with the catalyst provide an excellent pigment for coatings, dyes, paints and inks. The powder can be used as a pigment base for a variety of different emulsions. Various emulsions are available, for example, from Insignia Specialty Coatings, LLC, P.O. Box 231, El Dorado, Kans. 67042. A suitable emulsion for a paint, dye, coatings or ink preferably encapsulates the tungsten trioxide microparticles or nanoparticles to insulate them from atmospheric contamination, but, when spread and dried on an object, should still be porous enough to allow hydrogen gas to penetrate encapsulation to reach the metal oxide and catalyst. Water-based emulsions for paints, inks, dyes and coatings appear to provide the best properties.

In another embodiment, typical pigments that are used in paints, such as titanium dioxide and aluminum oxide, can be coated or impregnated with the chemochromic microparticles or nanoparticles. In this fashion, titanium dioxide, aluminum oxide, or other normal pigmentation that can be added to paint is used as a support or substitute for the impregnation of chemochromic microparticles or nanoparticles. Small particles of titanium dioxide or aluminum oxide that approach the microparticle or nanoparticle size can be coated with tungsten trioxide using an impregnation technique. For example, a transition metal, such as tungsten, can be dissolved to form a solution, such as tungstic acid. The tungstic acid is then dissolved in a solvent, such as ethanol, acetone or isopropyl alcohol. A titanium dioxide or aluminum oxide powder of microparticles or nanoparticles is then added to the solution of the solvent in the tungstic acid. The mixture is placed in an oven at about 60 to 70° Celsius to dry for about 16 hours. Once the solvent evaporates, a coating of tungsten trioxide covers the titanium dioxide or aluminum oxide nanoparticles. The process of coating the catalyst on the tungsten trioxide can be performed using the same coating process as disclosed above, in a subsequent step, or simultaneously with the coating of the tungsten oxide on the nanoparticles. In this fashion, micro- or nano-size pigmentation particles, such as titanium dioxide and aluminum oxide can be coated with a chemochromic material that can be used in paints, dyes, coatings and inks.

In another embodiment, nanoparticles of tungsten trioxide may be made by gas-phase plasma reaction in a vacuum and subsequently coated with a partial layer of platinum or palladium catalyst by a chemical technique similar to that disclosed by S. H. Joo, S. J. Choi, et al., "Ordered Nanoporous Arrays of Carbon Supporting High Dispersions of Platinum Nanoparticles." *Nature*, Vol. 412, pp. 169-172, Jul. 12, 2001, for coating carbon arrays with platinum. Such nanoparticles of tungsten trioxide are typically about 50 nm in diameter and can be used as pigments in indicator paints, coatings and inks.

In another embodiment, nanoparticles of tungsten trioxide can be made in the manner similar to the way in which nanoparticles for sol gel films are made. The process basically comprises oxidation of finely divided tungsten metal powder or other transition metal powder to produce tungsten trioxide powder or other transition metal oxide powder. Finely divided tungsten metal powder is available at many chemical warehouses. The tungsten metal powder may have a 100 or 200 mesh size. The tungsten metal powder is then reacted with hydrogen peroxide until the particles are oxidized and small enough that they become suspended in the liquid. The tungsten oxide particles are dissolved until they reach microparticle or nanoparticle size. At that point, finely divided platinum, i.e., platinum black, is added to the solution to stop the reaction. The solution is then filtered to obtain the microparticles or nanoparticles of tungsten trioxide. These tungsten trioxide microparticles or nanoparticles are then coated or impregnated with a catalyst.

In another embodiment, manufacturing nanoparticles of tungsten oxide can be done using a process of spray pyrolysis. To create tungsten trioxide, a solution, such as tungstic acid or other soluble form of tungsten, such as sodium tungstate in a soluble form, can be used to generate a fine mist of a tungsten solution. Various soluble tungsten solutions can be used for this process. The fine mist is then sprayed into a high temperature furnace so that the individual droplets react to form an oxide. In this fashion, very small tungsten trioxide particles that have microparticle or nanoparticle sizes can be made using the spray pyrolysis technique.

Various emulsions that are used in paints, dyes, coatings and inks provide a level of protection to the chemochromic materials to protect the catalyst layer from contaminants, as explained above. In applications where an emulsion does not provide such a protective layer, micro-encapsulation techniques can be used to encapsulate the micro-particles. The process of micro-encapsulation provides a protective polymer coating, such as PTFE or polyethylene, that encapsulates the microparticles or nanoparticles. Standard processes of using an emulsion of PTFE or other protective coating can be used to micro-encapsulate the microparticles or nanoparticles and thereby protect catalyst layers from contamination.

Key to the proper function of a visual indicator for hydrogen is the kinetics of its response and how these kinetics change over the useful life of the indicator. Different applications for the indicator will have different requirements for both speed and durability. Dynamic measurements of the changes in optical absorption of prototype indicators have been made as these chemochromic indicators are exposed to different concentrations of hydrogen gas mixtures, as explained in the example I above. Understanding and guidance in the development of products have been provided by analyzing these response curves in detail and fitting them to mechanistic models. The basic measurement that is made in these analyses is a recording of the optical transmittance of a test coupon as it is exposed to hydrogen. The sample is housed in a simple fixture that clamps the sample between a backing plate and an o-ring sealed chamber of less than one cubic centimeter volume. A gas mixture is fed through the chamber from a manifold of mass-flow controllers. Each of the controllers controls the flow of a different gas from the bank of compressed gas cylinders so that the desired mixture may be reproducibly applied to the sample chamber.

Figure 5:
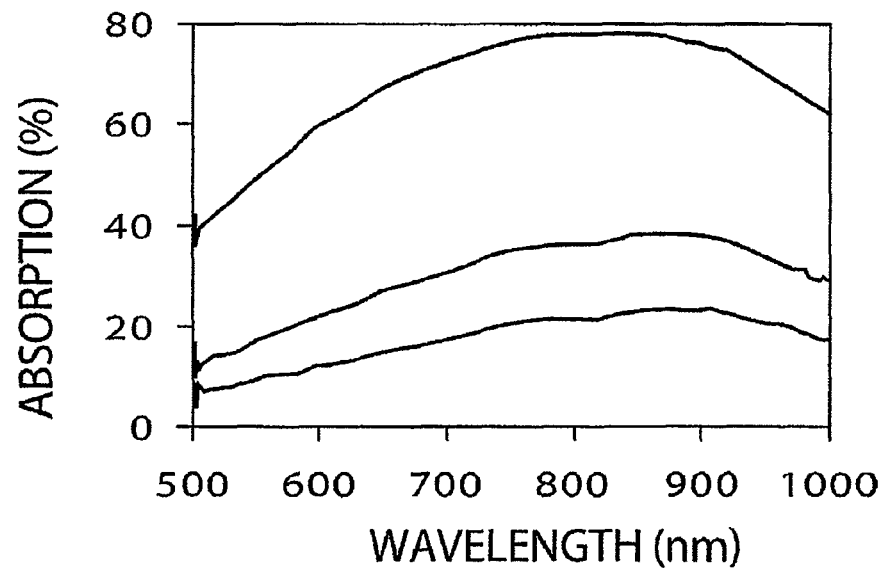
FIG. 5 is a graph illustrating the optical absorption of an indicator film at intervals during brief exposure to hydrogen.

The optical transmittance is measured with a spectrometer that is capable of measuring and recording the full spectrum from about 500 nm to 1100 nm each fraction of a second repeatedly throughout the exposure period. A white light source is directed to the sample by an optical fiber and the transmitted beam is collected by another optical fiber connected to the optical spectrometer. Because the optical absorption spectrum of the sample is so broad and changes primarily in amplitude rather than in spectral detail, it is sufficient to make dynamic measurement at a single wavelength. A measurement wavelength of 800 nm is utilized because this wavelength is near the peak of the absorption band, as indicated in FIG. 5.

Figure 6:
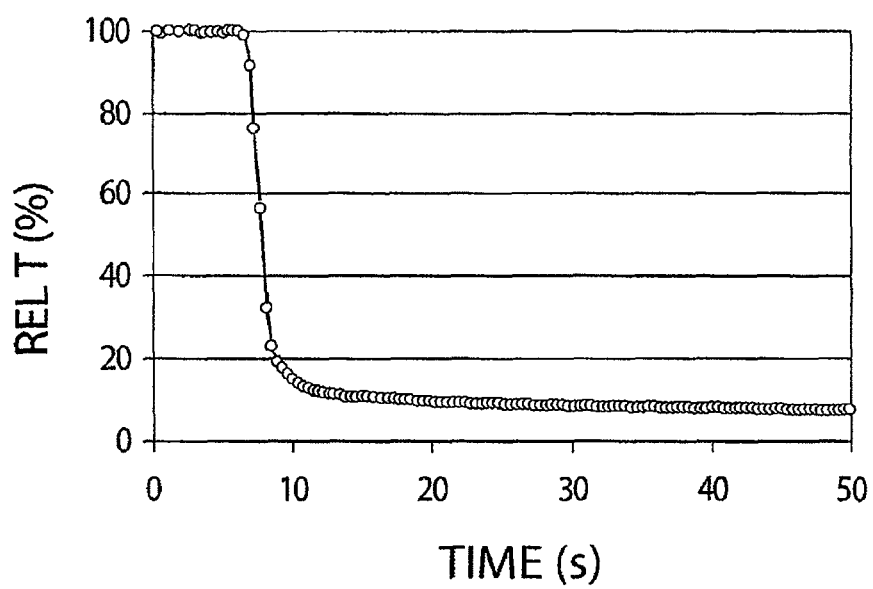
FIG. 6 is a graph illustrating the transmittance of nanopowder $WO_3$:Pt dispersed on a filter paper and exposed to 0.5% $H_2/N_2$ mixture.

FIG. 6 shows a typical recording of transmittance versus time for a nanoparticle $WO_3$:Pt powder dispersed on a filter paper. The transmittance of the sample decreases as the sample becomes more deeply colored. The rate of change in the transmittance reflects the rate of chemical reaction occurring in the $WO_3$.

The chemical reaction in a hydrogen/air mixture can be represented as:

$$Pd + xH_2 + x/4 O_2 + WO_3 \leftrightarrow H_xWO_3 + x/2 H_2O + Pd \quad \text{Eq. 1}$$

From the simple nature of the chemical reaction the rate is expected to be first-order and the response is expected to exhibit an exponential shape as indeed it does. The recording may be fit to an exponential function to determine a characteristic time constant for the reaction. The simplest fitting function is:

$$T(t) = T_0 + A_1 \exp(-(t-t_0)/\mathrm{tau}) \quad \text{Eq. 2}$$

Where the time constant, tau, is the time it takes for the transmittance to change by $1/e = 1/2.718 = 0.37$ of the total maximum change in transmittance. The time constant for the powder sample in FIG. 6 is 0.78 seconds.

The maximum change in transmittance will depend upon the thickness of the $WO_3$ layer in the indicator as well as the concentration of the hydrogen in the gas mixture.

Figure 7:
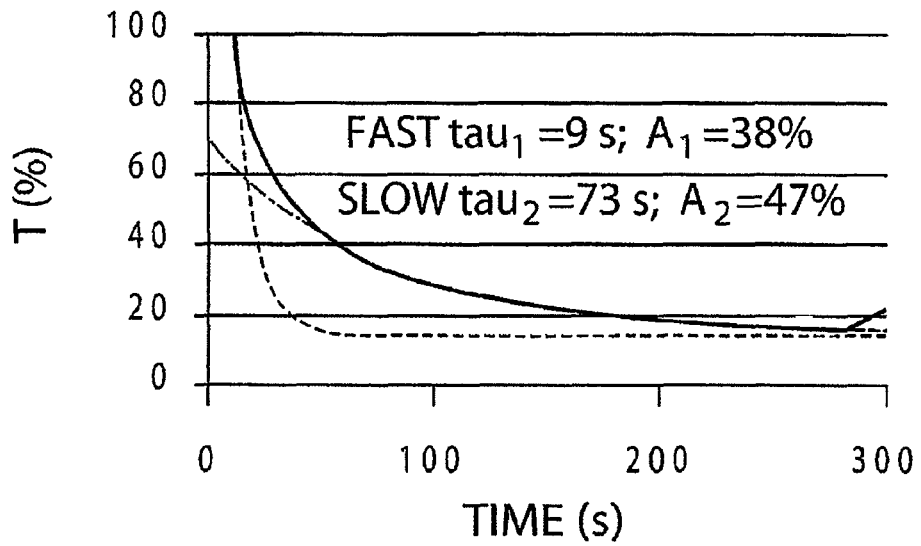
FIG. 7 is a graph illustrating the response time of a thin film indicator to 0.5% $H_2/N_2$ showing both fast and slow components.

Most of the indicators have a somewhat more complex response. FIG. 7 shows another indicator response measurement that is better fit by a combination of two different exponential functions:

$$T(t) = T_0 + A_1 \exp(-(t-t_0)/\mathrm{tau}_1) + A_2 \exp(-(t-t_0)/\mathrm{tau}_2) \quad \text{Eq. 3}$$

This kind of response function is characteristic of two parallel first-order reactions, i.e., a faster reaction and a slower reaction.

The two different reaction rates occur because there are two different kinds of sites where the hydrogen actually reacts with the $WO_3$. The hydrogen gas first reacts with the catalyst where the hydrogen gas dissociated into atomic hydrogen. This atomic hydrogen may diffuse through the catalyst to the catalyst/$WO_3$ interface and react there, or the atomic hydrogen may diffuse over the surface of the catalyst and react at the edge of the catalyst island where the free surface of the catalyst meets the free surface of the $WO_3$. These two different kinds of reaction sites are expected to have significantly different reaction kinetics.

Figure 8:
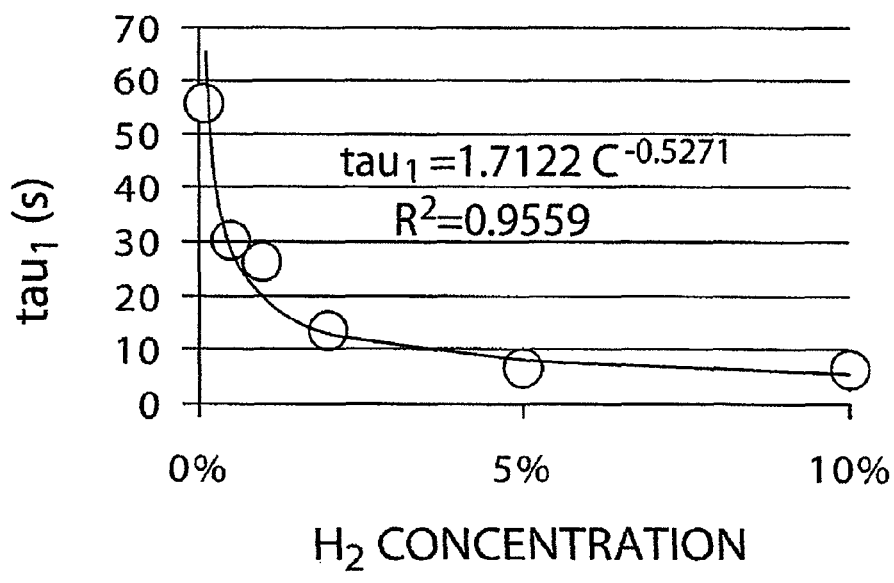
FIG. 8 is a graph showing that the speed of response is proportional to the square root of the hydrogen concentration.

As is to be expected from the simple chemical reactions, the speed of reaction increases with hydrogen concentration (e.g. the time constant decreases). FIG. 8 shows the measured time constant as a function of hydrogen concentration. The speed of response is proportional to the square root of the hydrogen concentration as would be expected from the hydrogen molecule dissociation step in the reaction (Eq. 1).

Figure 9:
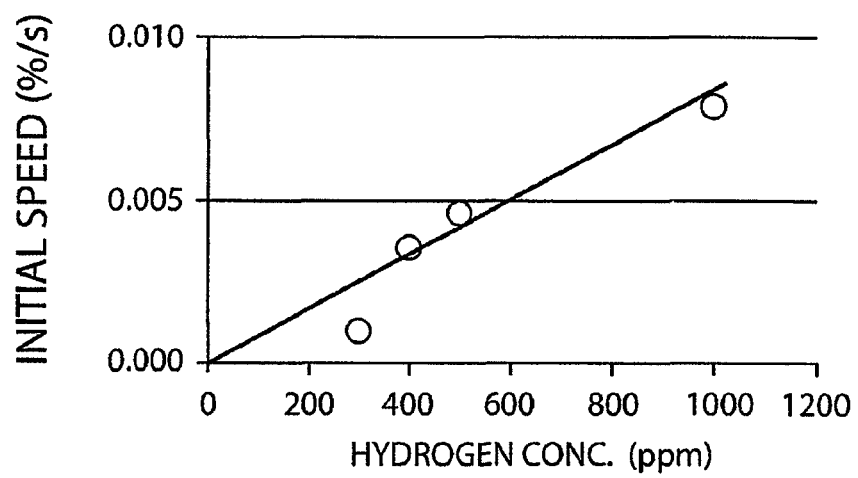
FIG. 9 is a graph illustrating the response limit of thin film indicators near 300 ppm $H_2$ in air.

The response becomes slower and slower as the hydrogen concentration is decreased and exhibits a lower response limit of about 300 ppm $H_2$ in air as shown in FIG. 9.

Figure 10:
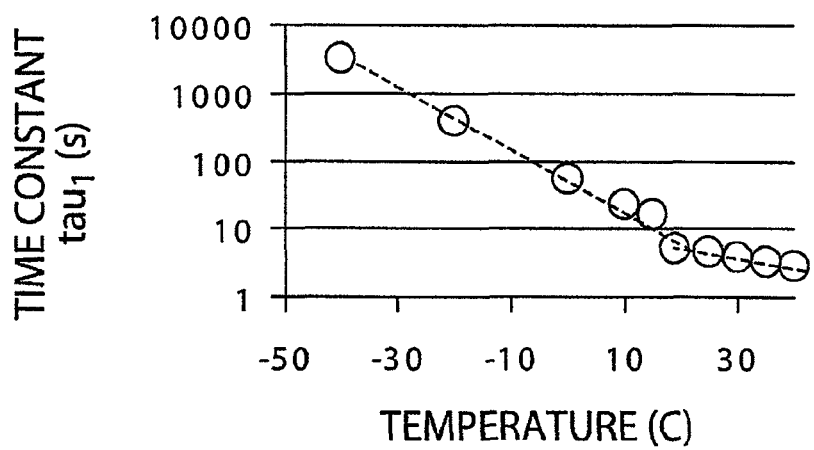
FIG. 10 is a graph illustrating the temperature dependence of the response of the chemochromic nanoparticle indicators.

The reaction rate also increases with temperature, as would be expected. FIG. 10 shows that the temperature dependence changes at around 15 C, i.e., the dependence changes more rapidly at lower temperatures than at higher temperatures.

Figure 11:
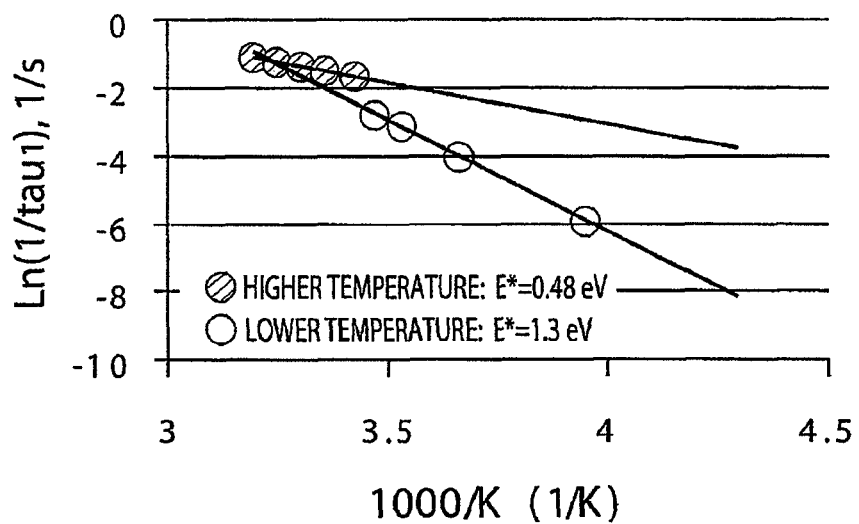
FIG. 11 is an Arrhenius plot of the response speed of the sensors versus inverse temperature for a high temperature and a low temperature.

If we plot this same data on a log scale versus reciprocal temperature, as shown in FIG. 11, the two segments of temperature dependence illustrate two different thermal activation energies, i.e., a higher energy barrier for the reaction at temperatures below 15 C and a lower barrier above 15 C. The change may be due to the presence of a layer of water on the surface of the indicator at temperatures below the dew point. The water forms as a result of the reaction (Eq. 1) and may retard the further reaction of the hydrogen by competing for reaction sites on the catalyst surface and also by favoring the back reaction.

If an indicator is stored in a sealed container (such as a resealable polypropylene bag), it changes very little over time or not at all. However, if an indicator is exposed to the environment for a long period of time, its response slows significantly. This slowing is, at least in part, due to contamination by chemicals in the environment that adsorb strongly to the catalyst and block subsequent hydrogen reactions. Chemicals that are known to be particularly troublesome are sulfur bearing compounds such as $H_2S$, mercaptans and thiols, some hydrocarbons, and CO. The very thin PTFE top layer of the indicators helps to retard such contamination but does so imperfectly. Thicker protective layers and more dense protective layers applied by chemical vapor deposition slow the rate of contamination more, but also slow the indicator response.

Figure 12:
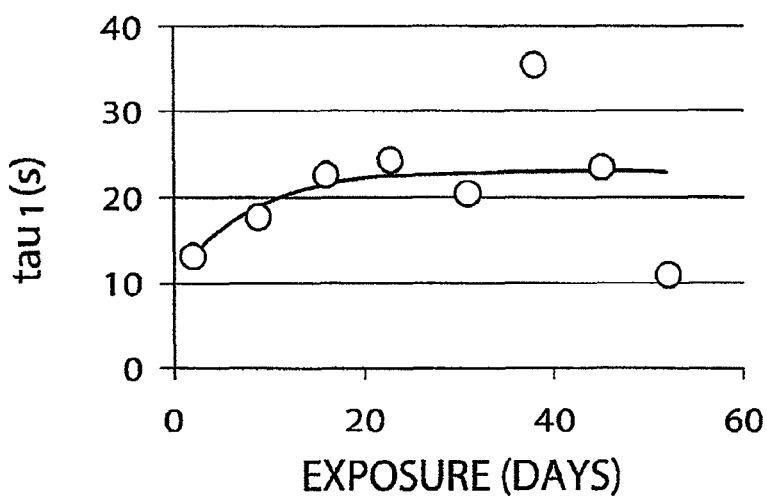
FIG. 12 is a graph that illustrates the change in the response speed of the sensors as a result of exposure to laboratory air.

FIG. 12 shows the trend of a thin film indicator's time constant over several weeks during which it was exposed to the laboratory air. There is a significant and variable change in the response time constant. Sometimes the variability can be associated with the changes in the chemicals being used in adjacent laboratory spaces. For example, a sudden increase in time constant was noted when a fellow chemist used thiols in a fume hood within our laboratory (see the data points at days 38 and 52). The time constant increased by more than 50% over a couple of days and then paradoxically recovered to a faster response within a couple of weeks. This kind of behavior is probably due to the reversible catalyst contamination by the errant thiol vapors.

If the degradation in response speed is primarily due to catalyst "poisoning," then the progress of degradation over time in a particular environment may be anticipated. Assuming the concentration of the contaminant(s) were constant over time or that the daily average concentration of contaminates stayed fairly constant over time, the fraction of remaining un-poisoned catalyst sites attacked each day would be approximately constant. That is, the relative rate of decrease in speed should be constant. Under these conditions the speed should slow at an ever decreasing rate and asymptotically approach a limiting speed as all of the susceptible catalytic sites became blocked by contaminants. This kind of behavior is common and fits a well known functional relationship:

$$\mathrm{tau} = \mathrm{tau}_0 + B_1(1 - \exp(-\mathrm{days}/tau_x)) \quad \text{Eq. 4}$$

This function is fit to the data in FIG. 12. While the variability in the data is too great for a very good fit, the trend of the data appears to be consistent with the fitted function.

Figure 13:
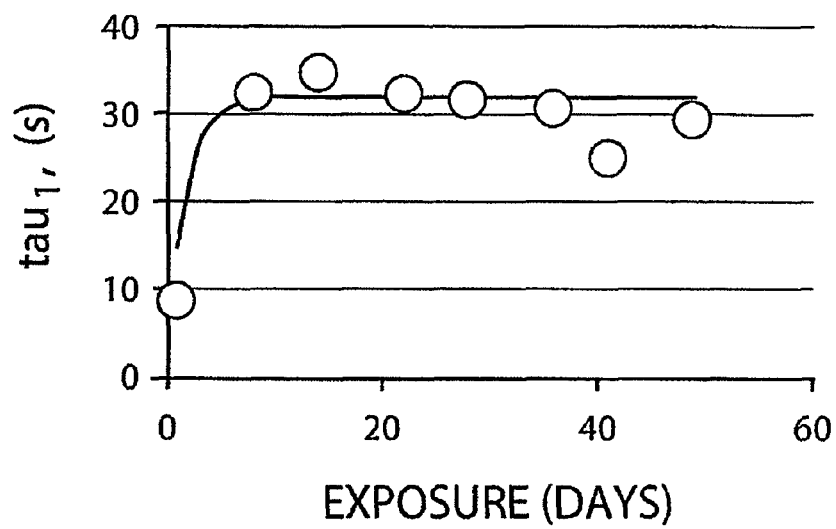
FIG. 13 is a graph illustrating the response time constant of a thin film indicator exposed to laboratory air and tested in 0.5% $H_2/N_2$.

FIG. 13 shows another set of measurements of thin film indicators of slightly different design. The thin film indicators were also exposed to laboratory air and were tested in 0.5% $H_2/N_2$ mixture.

Figure 14:
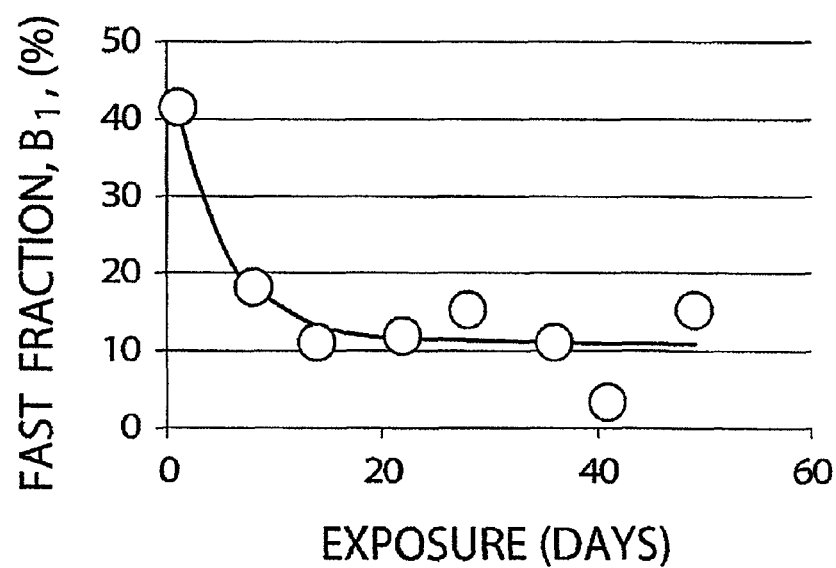
FIG. 14 is a graph illustrating the fraction of response associated with the fast reaction, B1.

The fraction of the response that is due to the fast reaction component, the parameter $A_1$ in Eq. 3, represents the fraction of available fast reaction sites and by the same argument is also expected to follow a functional form like Eq. 4. FIG. 14 shows the measured parameter B1 and the fit to Eq. 4.

The ability to extrapolate short term testing results to longer time periods is helpful in determining long term results.

While several applications for these visual indicators do not require long term exposure to the environment, it is desirable to develop other indicators with long useful lives. Reliance upon abbreviated exposure tests to provide long term predictions will allow new designs to be developed without the necessity of waiting to determine if such new designs are viable alternatives. If mechanistically reasonable trend functions can be fit to short term data, then the extrapolation of these functions to provide useful estimates of long term behavior can reasonably be expected.

Mechanistic functions are disclosed above that seem to fit measured trends of response speed versus temperature and response speed versus hydrogen concentration and a trend of response speed versus exposure time in the environment. As indicated in Eq. 3, the response speed of an indicator fits a double exponential with four parameters, $A_1$, $A_2$, $tau_1$ and $tau_2$. If the trends of these parameters can be established within a short period of time, then extrapolation of these trends can be made and estimates can be made of the longer term behavior of the sensors.

Figure 15:
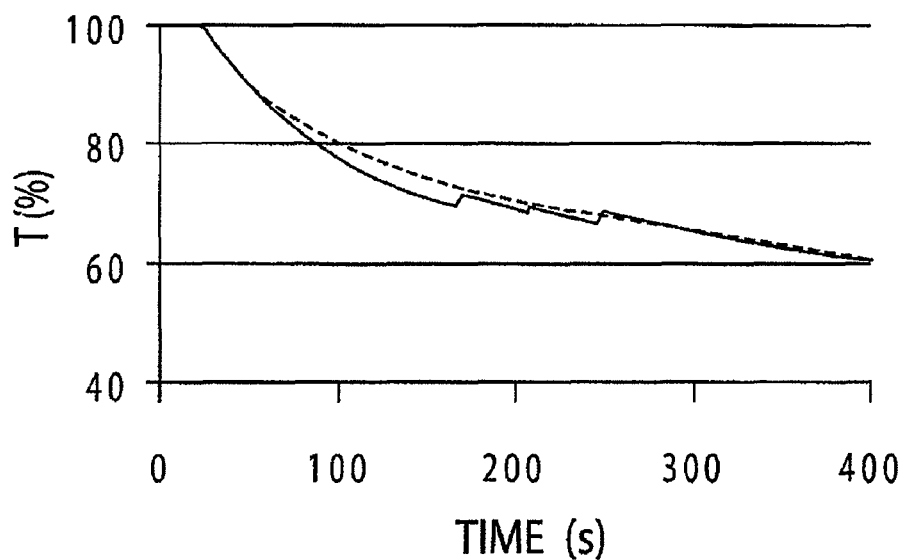
FIG. 15 is a graph showing the projected and measured performance after 49 days of laboratory exposure of the sensor materials.

This has been done for the indicator used to obtain the data in FIGS. 13 and 14. FIG. 15 shows the measured response for this indicator after 49 days of exposure compared to the response calculated from the parametric model. The agreement is somewhat fortuitous but encouraging.

Figure 16:
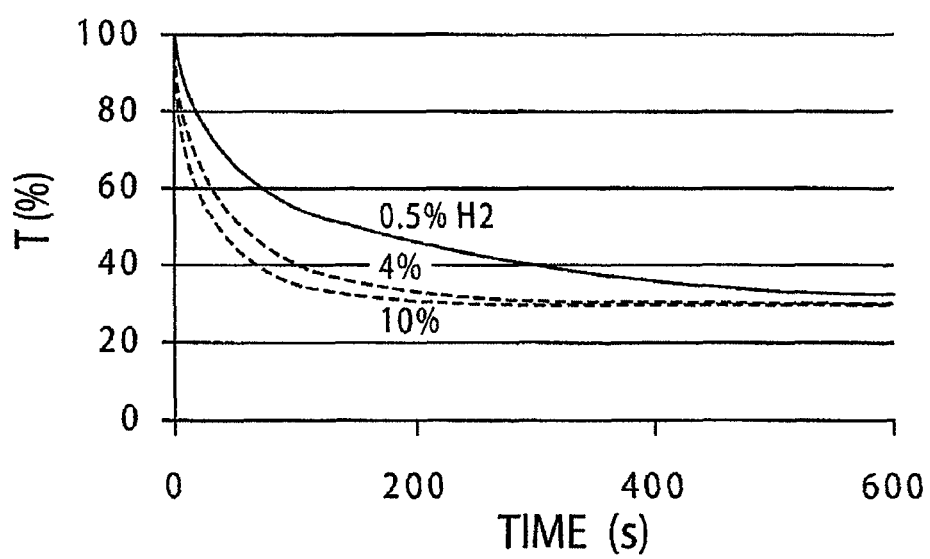
FIG. 16 is a graph illustrating the estimated response curves after one year of exposure to laboratory air, based on parametric projections.

The curve fits for response speed versus hydrogen concentration and temperature can be used to estimate response speed under different conditions. For example, FIG. 16 shows the predicted response of this same sensor after 365 days exposure and exposed to different hydrogen concentrations of 0.5%, 4% and 10%.

Prototype visual indicators of gaseous hydrogen have been developed and characterized. Thin film tungsten oxide coatings on transparent polymers are suitable for indicating the presence of hydrogen at concentrations well below safe limits. In applications where the indicator film need not be exposed to the environment for many days, the response of these indicators is fast and reliable.

The present developmental devices react to the presence of hydrogen slower if they are exposed to the environment for long periods of time. The rate of slowing depends upon the nature of the environment as well as the design of the indicator. Improvement of the stability of the indicator has been achieved through use of the techniques developed to estimate long term performance from short term environmental test results. This ability should help in the design indicators with suitable durability for additional applications in various demanding environments.

Microparticle or nanoparticle $WO_3$:Pt powder is an excellent indicator pigment for paints, dies, coatings and inks. The chemochromic nanoparticles are easy to use as pigments in various types of emulsions and coatings. The chemochromic nanoparticles can be incorporated into many commercially available specialty coatings, paints, inks and dyes and applied as these products are normally applied. The visual sensors that can be constructed using the chemochromic nanoparticles are very inexpensive compared to bulky electronic sensors. As a result, the sensors reduce the risk to people and property by continuously indicating the presence or absence of leaking hydrogen. The nanoparticles are made to have a long life because of the mechanical durability and resistance to degradation in environments containing many pollutants.

The foregoing description of the invention has been presented for purposes of illustration and description. It is not intended to be exhaustive or to limit the invention to the precise forms disclosed, and other modifications and variations may be possible in light of the above teachings. The embodiments were chosen and described in order to best explain the principles of the invention and its practical applications to thereby enable others skilled in the art to best utilize the invention in various embodiments and various modifications as are suited to the particular uses contemplated. It is intended that the appended claims be construed to include other alternative embodiments of the invention except insofar as limited by the prior art. The words "comprise," "comprises," "comprising," "include," "including," and "includes" when used in this specification, including the features, are intended to specify the presence of stated features, integers, components, or steps, but they do not preclude the presence or addition of one or more other features, integers, components, steps, or groups thereof. Also, it is recognized that exact sizing of all particles in a powder is not practical or even possible, which does not detract from the essence of this invention. Therefore, when powder particle, microparticle, and nanoparticle sizes or size ranges are described, specified, or claimed herein, it is understood that not every particle, microparticle, or nanoparticle in a powder can or will be in such sizes or size ranges, it being sufficient to meet the criteria that more of the particles in the powder are within such sizes or size ranges than the particles in the powder that are not within such sizes or size ranges. Also, while specific examples have been described using specific chemochromic metal oxides, e.g., tungsten oxides, and specific noble or precious metal catalysts, e.g., platinum, palladium, ruthenium, and mixtures thereof, persons skilled in the art are familiar with the chemochromic characteristics of other known chemochromic metal oxides, including molybdenum oxide and niobium oxide, as well as with other catalyst metals that perform for this function. Therefore, such known chemochromic metal oxides and catalysts can be predicted and expected by persons skilled in the art to work for hydrogen sensing pigment applications according to this invention and need not be proven by experimentation and example to come within the scope of this invention. Also, when particles, microparticles, or nanoparticles of a metal oxide material are described, specified, or claimed herein, such description, specification, or claim does not include substrates of other inert or non-chemochromic material on which a chemochromic metal oxide has been deposited or coated. Also, when particles, microparticles, or nanoparticles of a metal oxide material are described, specified, or claimed herein, such description, specification, or claim means discrete particles, microparticles, or nanoparticles, not a solid layer comprising particles, microparticles, or nanoparticles that have been thermal processed or otherwise fused together into solid layers.

What is claimed is:

1. A method of making a hydrogen sensing pigment for use in paints, inks, dyes, and powder coating materials, comprising:
   mixing powder nanoparticles of metal catalyst material with powder microparticles of chemochromic metal oxide material; and
   superficially coating the powder microparticles of chemochromic material with the nanoparticles of the metal catalyst material by winding or milling the nanoparticles of metal catalyst material with the microparticles of chemochromic metal oxide material.

2. The method of claim 1, wherein the microparticles of chemochromic metal oxide material are less than 100 microns in diameter.

3. The method of claim 1, wherein the nanoparticles of metal catalyst material are sized in a range of a few nanometers to a few tens of nanometers.

4. The method of claim 1, wherein the microparticles of chemochromic metal oxide material are sized in a range of 10 to 100 microns in diameter.

5. The method of claim 1, wherein the nanoparticles of metal catalyst material are sized in a range of a 2 nanometers to 30 nanometers.

* * * * *